United States Patent [19]

Owens

[11] 4,356,118

[45] Oct. 26, 1982

[54] TRYPTOPHAN DERIVATIVES

[75] Inventor: William H. Owens, Arlington Heights, Ill.

[73] Assignee: G. D. Searle & Co., Skokie, Ill.

[21] Appl. No.: 269,202

[22] Filed: Jun. 2, 1981

[51] Int. Cl.³ .......................................... C07C 103/52
[52] U.S. Cl. ........................................... 260/112.5 R
[58] Field of Search ................... 424/177; 260/112.5 R

[56] References Cited

U.S. PATENT DOCUMENTS

| | | | |
|---|---|---|---|
| 4,146,611 | 3/1979 | Ondetti et al. | 424/177 |
| 4,154,960 | 5/1979 | Ondetti et al. | 424/177 |
| 4,156,786 | 5/1979 | Ondetti et al. | 424/177 |
| 4,179,434 | 12/1979 | Ondetii et al. | 424/177 |

OTHER PUBLICATIONS

G. R. Pettit, "Synthetic Peptides", I, (1971), pp. 86, 87, 124–127, 136, 137, 170, 171, 204 & 205.
G. R. Pettit, "Synthetic Peptides", II, (1973), pp. 60, 68, 69.
G. R. Pettit, "Synthetic Peptides", III, (1978), pp. 138, 139.
G. R. Pettit, "Synthetic Peptides", IV, (1977), pp. 128, 129, 160, 161.
G. R. Pettit, "Synthetic Peptides", V, (1980), pp. 150, 151, 170, 171, 186, 187.

*Primary Examiner*—Delbert R. Phillips
*Attorney, Agent, or Firm*—James G. Passe

[57] ABSTRACT

The invention provides certain substituted tryptophan derivatives of Formula I which are useful for alleviating or reducing angiotensin related hypertension in hypertensive mammals.

14 Claims, No Drawings

TRYPTOPHAN DERIVATIVES

BACKGROUND OF THE INVENTION

The present invention provides novel compounds. In particular the present invention relates to novel tryptophan derivatives of formula I which are useful for reducing or relieving angiotensin related hypertension.

Angiotensin II is a powerful vasoconstrictor agent that has been implicated as the main causative agent in the etiology of renovascular hypertension.

Angiotensin II is formed from angiotensin I by the action of angiotensin converting enzyme. Angiotensin I is a biologically inert decapeptide cleaved from the blood protein angiotensinogen by the action of the enzyme renin [Oparil et al., New England J. of Med., 291, 389–401 (1974)]. Angiotensin converting enzyme and renin are also biologically inert.

Angiotensin converting enzyme is also responsible for the inactivation of bradykinin, a vasodilator agent that has been implicated in the regulation of renal function [Erdos, Circulation Research 36,247 (1975)].

Agents that inhibit angiotensin converting enzyme can therefore counteract the indirect pressor effect of angiotensin I since this is due only to its conversion to angiotensin II. These agents can be used therapeutically in the treatment of forms of renovascular and malignant hypertension as well as other forms of angiotensin dependent hypertension [Gavras et al., New England J. of Med., 291 817 (1974)].

According to Oparil et al, supra, angiotensin II has a major role in maintaining circulatory homeostasis in the sodium depleted animal, but in the normal animal on a normal salt intake, angiotensin II is not required for the acute maintenance of blood pressure. In a variety of conditions that stress the renin-angiotensin system, acute administration of an Angiotensin Converting Enzyme inhibitor or an angiotensin II blocker lowers blood pressure and causes a rise in plasma renin activity.

Certain mercaptoacyl amino acids have been disclosed in the literature. U.S. Pat. No. 3,246,025, Apr. 12, 1966, shows mercatopropionyl glycine derivatives which are useful for strengthening function of the liver and as antidotes for such poisons as mercury and organoarsenic compounds. See also German Offenlegungsschrift No. 2,349,707, U.S. Pat. No. 3,897,480, July 29, 1957 shows N (α-mercaptoacyl)amino acids useful for prophylaxis and therapy in treating a metabolic disorder, such as nosotoxicosis due to a heavy metal, radiation disorder, diabetes or hepatitis, U.S. Pat. No. 3,857,951, Dec. 31, 1974, shows the use of 2-mercaptopropionylglycine and its alkali metal salts in treating respiratory diseases.

It has been reported that 2-mercaptopropionyl glycine, known as a liver protecting agent, produced lowering of the blood pressure upon intravenous injection to anesthetized normotensive rats [Schulze, Arznem Forsch, 22, 1433 (1972)], an unreliable model [Schwartz, Methods in Pharmacology, Vol. I, 125 (1971); Berger, Selected Pharmacological Testing Methods, Vol. 3, 171, 194 (1968)]; while others have reported no noticeable effects on blood pressure, etc. [Fujimura et al., Nippon Yakurigaku Zasshi 60, 278, 92 (1964)]. See also Ripa, Proc. Int. Symp. Thiola, Osaka, Japan 1970, p. 226–230, who reported that in normotensive rats mercaptopropionylglycine increases angiotensinogen and lowers renin blood levels by a feedback homeostatic mechanism.

A variety of dipeptides are known as shown in the text Pettit, *Synthetic Peptides*, Vol. I (1971), e.g., pages 94–104. Additionally, foodstuff additives are shown, for example, in the following U.S. Pat. Nos. 2,851,482, L-argininyl-L-glutamate; 3,799,918, alkyl esters of α-aspartyl-α-alkyl aliphatic amino acid dipeptides; 3,952,115, N-acyl-L-methionine ester, N,N'-diacyl-L-glycylmethionine and methionylglycine; and 4,024,286, dipeptides of methionine with glycine, valine, alanine or glutamic acid.

PRIOR ART

Pharmacologically active compounds for treating hypertension are known as described above. Additionally, in U.S. Pat. No. 4,177,277 a method for alleviating hypertension in mammals by administration of an amino acid derivative is described. Further, Japanese Pat. Nos. 089215 (Derwent Abstract 19283C/1) and 082809 (Derwent Abstract 09529C/06) describe mercapto-amino acids which are useful as antihypertensives.

SUMMARY OF THE INVENTION

The present invention particularly provides a compound according to formula I:

wherein $R_1$ is:
(a) hydrogen; or
(b) methyl;
wherein $R_2$ is:
(a) hydrogen;
(b) iso-propyl; or
(c) tert-butyl;
wherein $R_3$ is:
(a) methyl; or
(b) $NR_5H$;
wherein $R_5$ is:
(a) hydrogen; or
(b) aroyl;
wherein $R_4$ is:
(a) $CH_2SH$;
(b) iso-propyl;
(c) iso-butyl;
(d) imidazolmethyl;
(e) phenylmethyl; or
(f) methylthioethyl.

The blocking of the conversion of Angiotensin I to Angiotensin II is a known powerful method of controlling certain forms of hypertension. The following two procedures are used in the rat to test for in vivo converting enzyme blocking activity and therefore antihypertensive activity of the invention compounds. These procedures have been verified through the testing of the known converting enzyme blocker Captopril.

Two normotensive rats at a time were anesthetized with 1.5 g/kg urethane IM and cannulated with Tygon tubing (0.040"×0.025") via the left carotid for blood pressure monitoring. The right jugular vein was doubly cannulated (Tygon 0.030"×0.010") for Angiotensin I injections and for the test compound. The rats were tracheotomized and cardiovascular reflexes blocked with pentolinium tartrate (5 mg/kg i.m.).

Procedure 1

Infusion of Compound

Following surgery the animals were allowed to stabilize for 30 minutes. Three challenge doses of Angiotensin I (500 ng/kg i.v. in a volume of 0.01 ml/100 g) were administered at three minute intervals before treatment to establish the diastolic blood pressure responses. After reestablishing a baseline BP the test compound was infused for a 10 min. period at a rate of 0.05 ml/min. Probe dosing with Angiotensin I was repeated 2,4, and 8 minutes after starting the infusion. If the response to AI was not abolished by the initial 10 minute infusion, the rate of infusion is doubled (0.1 ml/min) and maintained for an additional ten minutes. The AI challenges were repeated 2, 4 and 8 minutes into the second infusion period. Rates higher than 0.1 ml/min were not used. At the end of the infusion the probe doses of AI were given at 5 min intervals for 30 minutes to estimate the rate of inactivation of the compound.

Procedure 2

Bolus Injections

The animals were surgically prepared as described in Procedure 1 and allowed to stabilize for 30 min. Pretreatment blood pressure responses to injections of AI (500 ng/kg i.v.) were obtained before administration of test compound. After recovering to base line a bolus injection of the test compound was given. Probe dosing with AI was done at 2, 5, 10 min after the antagonist injection. Twelve minutes after the first injection a predetermined higher dose of the drug was given and the probe dosing of AI were repeated. This sequence is repeated for a total of three doses of the drug. In some animals two doses of AII (200 ng/kg) were given before the start of the AI injections and after completion of the sequence to test for specificity of the response.

By virtue of this antihypertensive activity the compounds of formula I are useful in treating hypertensive symptoms in humans and animals. A physician or veterinarian of ordinary skill could readily determine a subject who is exhibiting hypertensive symptoms. Regardless of the route of administration selected, the compounds of the present invention are formulated into pharmaceutically acceptable dosage forms by conventional methods known to the pharmaceutical art.

The compounds can be administered in such oral unit dosage forms as tablets, capsules, pills, powders, or granules. They also may be administered rectally, or vaginally in such forms as suppositories, creams, ointments or bougies; they may also be introduced in the form of eye drops, intraparenterally, subcutaneously, intramuscularly, or intravenously, using forms known to the pharmaceutical art.

An effective but non-toxic quantity of the compound is employed in treatment. The dosage regimen for preventing or treating hypertension by the compounds of this invention is selected in accordance with a variety of factors including the type, age, weight, sex, and medical condition of the mammal, the severity of the hypertension, the route of administration and the particular compound employed. An ordinarily skilled physician or veterinarian will readily determine and prescribe the effective amount of the anti-hypertensive agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 0.3 mg/kg up to at least 100 mg/kg orally. When other forms of administration are employed equivalent doses are administered. When dosages beyond 100 mg/kg are employed, care should be taken with each subsequent dose to monitor possible toxic effects.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of the instant invention are all prepared by the methods described in Charts A and B.

The thio compound of the instant invention is prepared as described on Chart A. DL-S-Acetyl-$\beta$-mercaptoisobutyric acid and N-methylmorpholine are cooled and isobutylchloroformate added. Then Val-Trp-methylester is added and the solution reacted, cooled and extracted to yield the formula II trytophan methylester. The formula II ester is then treated with a basic alcoholic solution and concentrated. The residue is then extracted to yield a formula III tryptophan derivative.

Chart B describes the process for producing the amino derivatives of the invention A t-butyl-oxycarbonyl-Val and N-Methyl-morpholine is reacted with isobutylchloroformate and then with L-Trp-methylester hydrochloride. This reaction yields the tryptophan methylester of formula XI. The formula XI methylester is then treated with anhydrous hydrochloric acid to yield the tryptophan methylester hydrochloride of formula XII.

A solution of t-butyloxycarbonyl-L-Leu and N-methylmorpholine is treated successively with isobutylchloroformate and the formula XII methylester to yield the formula XIII methylester. This methylester is then hydrolyzed in a basic alcoholic solution to yield the formula XIV tryptophan derivative. This can be treated with anhydrous acid to yield the formula XV tryptophan derivative.

DESCRIPTION OF THE PREFERRED EMBODIMENTS

The operation of this invention is further elaborated by the representative examples below:

EXAMPLE 1 t-butyloxycarbonyl-Valyl-tryptophan methyl ester (formula XI of Chart B: $R_2$ is isopropyl)

A tetrahydrofuran solution (60 ml) containing 3.4 g. (15.7 mmoles) of t-butyloxycarbnyl-Val and 3.3 ml (29.4 mmoles) of N-methylmorpholine is cooled to $-20°$ C. and 1.9 ml (14.8 mmoles) of isobutylchloroformate is added. The resulting suspension is stirred at $-20°$ C. for 5 minutes and 2.8 g (11.0 mmoles) of L-Trp-OCH$_3$-HCl is added. After stirring the reaction at $-20°$ C. for 3 hours, it is allowed to warm to room temperature and stirred overnight. It is then cooled to $0°$ C. and stirred for 30 minutes with 2 molar KHCO$_3$ and extracted with ethyl acetate. The organic layer is washed successively with 5 percent citric acid, water and saturated sodium chloride, then dried over a magnesium sulfate. Upon concentrating under reduced pressure, a solid is obtained which is crystallized from isopropanol to give 3.15 g (68 percent) of title compound. Structure supported by NMR.

EXAMPLE 2

Valyl-tryptophan methyl ester.HCl (formula XII of Chart B: $R_2$ is isopropyl).

A 3.1 g (7.43 mmoles) sample of the product of Example 1 is dissolved in 20 ml of acetic acid and treated with 11.3 ml (74.6 mmoles) of 6.6 N HCl in dioxane. After stirring the solution 10 minutes at room temperature, it is concentrated under reduced pressure at 40° C. and the residue obtained is triturated with ether to give 2.6 g (99 percent) of title compound. Analysis calculated for $C_{17}H_{20}N_3O_2HCl$ is C, 57.70; H, 6.84; N, 11.88. Found: C, 57.75; H, 6.84, N, 11.71. Structure supported by NMR.

EXAMPLE 3 t-butyloxycarbonyl-Leu-Val-Trp-methyl ester (formula 3 of Chart B: $R_2$ is isopropyl; $R_4$ is isobutyl).

A tetrahydrofuran solution (60 ml) containing 2.6 g (10.4 mmoles) of t-butyloxycarbonyl-L-Leu($H_2O$) and 2.2 ml (19.6 mmoles) of N-methyl-morpholine is cooled to −20° C. and 1.26 ml (9.68 mmoles) of isobutylchloroformate is added. The resulting suspension is stirred at −20° C. for 5 minutes and 2.6 g (7.37 mmoles) of title compound of Example 2 is added. After stirring the reaction at −20° C. for 3 hours, it is allowed to warm to room temperature and is stirred for an additional 2 hours. It is then cooled to 0° C., stirred for 30 minutes with 2 molar $KHCO_3$ and extracted with ethyl acetate. The organic layer is washed successively with 5 percent citric acid, water and saturated sodium chloride, dried over magnesium sulfate and concentrated under reduced pressure to give 3.9 g (100 percent) of title compound.

EXAMPLE 4 t-butyloxycarbonyl-Leucyl-Valyl-tryptophan (formula XIV of Chart B: $R_2$ is isopropyl; and $R_4$ is isobutyl).

A 3.0 g (5.66 mmoles) sample of title compound of Example 3 is dissolved in 12 ml of 95 percent ethanol and treated with 6 ml of 1 N sodium hydroxide. After stirring the solution at room temperature for 4 hours, it is concentrated under reduced pressure. The residue is dissolved in water, and the basic solution extracted with ether. The aqueous layer is acidified with 5 percent citric acid and extracted with ethyl acetate. The organic phase is washed with saturated sodium chloride solution, dried over a magnesium sulfate and concentrated under reduced pressure to give 2.6 g (90 percent) of the title compound.

EXAMPLE 5

Leucyl-Valyl-tryptophan hydrochloride (formula I of Chart A: $R_1$ is hydrogen; $R_2$ is isopropyl; $R_3$ is $NH_2$; $R_4$ is isobutyl).

To a 1.8 g (3.49 mmoles) sample of title compound Example 4 in 10 ml of glacial acetic acid is added 5.3 ml (35.0 mmoles) of 6.6 N HCl in a dioxane. The solution is stirred at room temperature for 10 minutes and concentrated under reduced pressure at 40° C. The residue is triturated with ether to give 1.4 g (89 percent) of the title compound.

EXAMPLE 6

N-[S-acetyl-β-mercaptoisobutyroyl]-valyl-tryptophan methyl ester (formula II of Chart A: $R_2$ is isopropyl).

A tetrahydrofuran solution (250 ml) containing 5.5 g (34.0 mmoles) of DL-S-Acetyl-β-mercaptoisobutyric acid and 7.7 ml (68.6 mmoles) of N-methylmorpholine is cooled to −20° C. and 4.2 ml (32.3 mmoles) of isobutylchloroformate is added. The suspension is stirred at −20° C. for 5 minutes and 10.0 g (28.3 mmoles) of Val-Trp-methylester HCl is added. After stirring the reaction at −20° C. for 2 hours at room temperature an additional 2 hours, it is cooled to 0° C., stirred for 30 minutes with 2 molar $KHCO_3$ and extracted with ethyl acetate. The organic layer is washed successively with 5 percent citric acid, water and saturated sodium chloride, dried over magnesium sulfate and concentrated under reduced pressure to give 11.5 g (88 percent) of title compound.

EXAMPLE 7

N-[N-(3-mercapto-2-methyl-1-oxopropyl)valyl]tryptophan (formula 1 of Chart A: $R_1$ is hydrogen; $R_2$ is isopropyl; $R_3$ is methyl; $R_4$ is $HSCH_2$).

A 5.5 g (11.9 mmoles) sample of the title compound of Example 6 is suspended in 95 percent ethanol (70 ml) and treated with 35 ml of 1 N sodium hydroxide. After stirring the reaction at room temperature for 4 hours it is concentrated under reduced pressure. The residue is dissolved in water and the basic solution extracted with ether. The aqueous layer is acidified with 10 percent HCl and extracted with ethyl acetate. The organic phase is washed with saturated sodium chloride solution, dried over magnesium sulfate and concentrated under reduced pressure. Following chromatography, one obtains 3.5 g (73 percent) of title compound.

EXAMPLE 8

N-[N(3-mercapto-2-methyl-1-oxopropyl)glycylm]tryptophan.

The title compound is prepared using the previously described procedures and the following reagents 3.0 grams (7.16, mmoles) N-(S-acetyl-β-mercaptoisobutyroyl)-glycyl-tryptophan methyl ester, 40 ml 95 percent ethanol, 21 ml 1 N NaOH. Yield total 1.1 gram (42 percent). Analysis calculated for $C_{17}H_{21}N_3O_4S$: C, 56.18; H, 5.82; N, 11.56; S 8.82. Found: C, 55.77; H, 5.80; N, 11.44; S, 8.87.

EXAMPLE 9

L-Leucyl-L-3-methyl-valyl-L-tryptophan hydrochloride.

The title compound is prepared using the previously described procedures and the following reagents: 0.45 grams (0.85 mmoles) t-butyloxcarbonyl-leucyl-3-methyl-valyl-tryptophan, 2.8 ml glacial acetic acid, and 1.4 ml of 6.07 N HCl in dioxane. Yield was 0.27 grams (67 percent). Analysis calculated for $C_{23}H_{34}N_4O_4 \cdot HCl \cdot H_2O$: is C, 56.96; H, 7.69; N, 11.55 found C, 57.26; H, 7.55; N, 11.16.

EXAMPLE 10

N-[N-(3-mercapto-2-methyl-1-oxopropyl)-3-methylvalyl]tryptophan.

The title compound is prepared using the previously described procedures and the following reagents: 0.90 g (1.89 mmoles) of N-(S-acetyl-β-mercaptoisobutyroyl)-3-methylvalyl-tryptophan methyl ester, 8 ml of 95 percent ethanol, 4.0 ml of 1 N NaOH. Chromatographed yield is 0.54 grams (63 percent). Analysis calculated for $C_{21}H_{29}N_3O_4S$: C, 60.12; H, 6.97; N, 10.02; S, 7.64. Found: C, 60.27; H, 7.14; N, 9.42; S, 7.25.

EXAMPLE 11

L-Phenylalanyl-valyl-tryptophan hydrochloride.

The title compound is prepared using the previously described procedures and the following reagants: 1.85 grams (3.4 mmoles) t-butyloxycarbonyl-phenylalanyl-valyl-tryptophan, 10 ml of glacial acetic acid and 7.25 ml of 6.07 N hydrochloric acid in dioxane. Yield is 1.6 g (100 percent). Analysis calculated for $C_{25}H_{30}N_4O_4 \cdot HCl \cdot 2H_2O$: C, 56.99; H, 6.93; N, 9.17. Found: C, 56.70; H, 6.43; N, 8.82.

EXAMPLE 12

L-Methionyl-L-valyl-L-tryptophan hydrochloride.

The title compound was prepared using the previously described procedure and the following reagants: t-butyl oxycarbonyl-methionyl-valyl-tryptophan (4.61 grams), 32 milliliters of glacial acetic acid and 17.5 ml (106.2 mmoles) 6.07 N hydrochloric acid in dioxane. Yield is 3.2 grams. Analysis calculated for $C_{21}H_{30}N_4O_4S \cdot HCL \cdot H_2O$: C, 51.57; H, 6.80; N, 11.46. Found: C, 51.29; H, 6.59; N, 11.72.

EXAMPLE 13

γ-[(methylsulfinyl)-L-α-aminobutyroyl-valyl]-L-tryptophan hydrochloride.

To a solution containing 1.0 grams (2.05 mmoles) of methionyl-valyl-tryptophan in 16 milliliters of water is added 0.8 ml of 10.4 N $H_2O_2$ solution (8.4 mmoles). The solution is stirred at room temperature for two hours and eluted with 75 ml of water. Solution is then lyopholized to give 0.60 grams (56 percent) of the title compound. Analysis calculated for $C_{21}H_{30}N_4O_5S \cdot HCl \cdot 2H_2O$: C, 48.22; H, 6.74; N, 10.71. Found: C, 48.34; H, 6.64; N, 11.32.

EXAMPLE 14

β-(methylthio-α-aminopropionoyl-valyl)-trytophan hydrochloride

The title compound was prepared using the previously described procedures and the following reagants: 2.37 grams (4.56 mmoles) t-butyloxycarbonyl-5-methyl-cysteinyl-valyl-tryptophan, 14.7 ml glacial acetic acid and 8 ml of 6.07 N HCl in dioxane total yield was 1.7 g (82 percent). Analysis calculated for $C_{20}H_{28}N_4O_4S \cdot HCl$: C, 52.5; H, 6.40; N, 12.26. Found: C, 52.73; H, 6.62; N, 11.95.

EXAMPLE 15

L-Histidyl-L-valyl-L-tryptophan dihydrochloride.

A 5.0 g (0.9 mmoles) sample of t-butyloxycarbonyl-histidyl-valyl-tryptophan methyl ester, which was prepared using the processes previously described, in 10 ml 1 N HCl is heated on a steam bath for two hours. The solvent is removed under reduced pressure and the residue dissolved in acetic acid and precipitated with ether. Yield of a solid was 0.44 grams (96 percent). Purified by counter current distribution in butyl alcohol, acetic acid and water to obtain 0.34 grams of the title compound. Analysis calculated for $C_{22}H_{28}N_6O_4 \cdot 2HCl \cdot 1\frac{3}{4} H_2O$: C, 48.49; H, 6.20; N, 15.42. Found: C, 48.27; H, 5.81; N, 15.25.

EXAMPLE 16

L-Valyl-valyl-tryptophan hydrochloride

The title compound was prepared using the previously described process using the following reagants: 0.85 grams (1.7 mmoles) t-butyloxycarbonyl-Valyl-valyl-tryptophan, 6 ml glacial acetic acid and 3 ml 5.68 N HCl in dioxane Total yield was 0.75 grams (100 percent). Anaylsis calculated for $C_{21}H_{30}N_4O_4 \cdot HCl \cdot \frac{1}{3} H_2O$: C, 56.69; H, 7.17; N, 12.59. Found: C, 57.06; H, 7.3; N, 12.17.

EXAMPLE 17

L-Isoleucyl-L-valyl-L-tryptophan hydrochloride.

The title compound is prepared using the previously described procedures and the following reagants: 1.17 g (2.3 mmoles) t-butyloxycarbonyl-isoleucyl-valyl-tryptophan, 10 ml glacial acetic acid and 10 ml 6.07 HCl in dioxane. Total yield was 0.91 g. (88 percent). Analysis calculated for $C_{22}H_{32}N_4O_4 \cdot HCl \cdot H_2O$: C, 56.10; H, 7.49, N, 11.90. Found: C, 56.34; H, 7.48; N, 11.72.

EXAMPLE 18

Benzoyl-phenylalanyl-valyl-tryptophan.

A mixture of 30 ml chloroform and 30 ml water containing 1.0 g of phenylalanyl-valyl-tryptophan and 0.6 g of sodium carbonate is cooled to 0° and treated with 0.20 ml of benzoyl chloride. The reaction mixture was allowed to warm to room temperature and stirred overnight. The layers were separated and the aqueous layer extracted with ethyl acetate. The combined organic phases were dried over magnesium sulfate and concentrated under reduced pressure to give 0.47 g (53 percent) of the title compound. Analysis calculated for $C_{32}H_{34}N_4O_5 \cdot H_2O$: C, 67.11; H, 6.34; N, 9.79. Found: C, 67.00; H, 6.23; N, 9.13.

EXAMPLE 19

Using the previously described processes and appropriate starting materials the following compounds may be prepared.

Benzoyl-methionyl-valyl-tryptophan
N-Benzyl-cysteinyl-valyl-tryptophan

CHART A

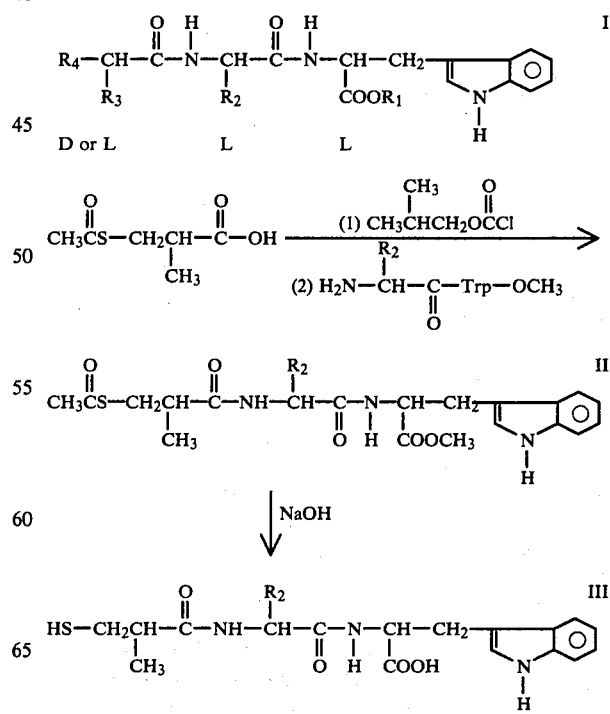

CHART B
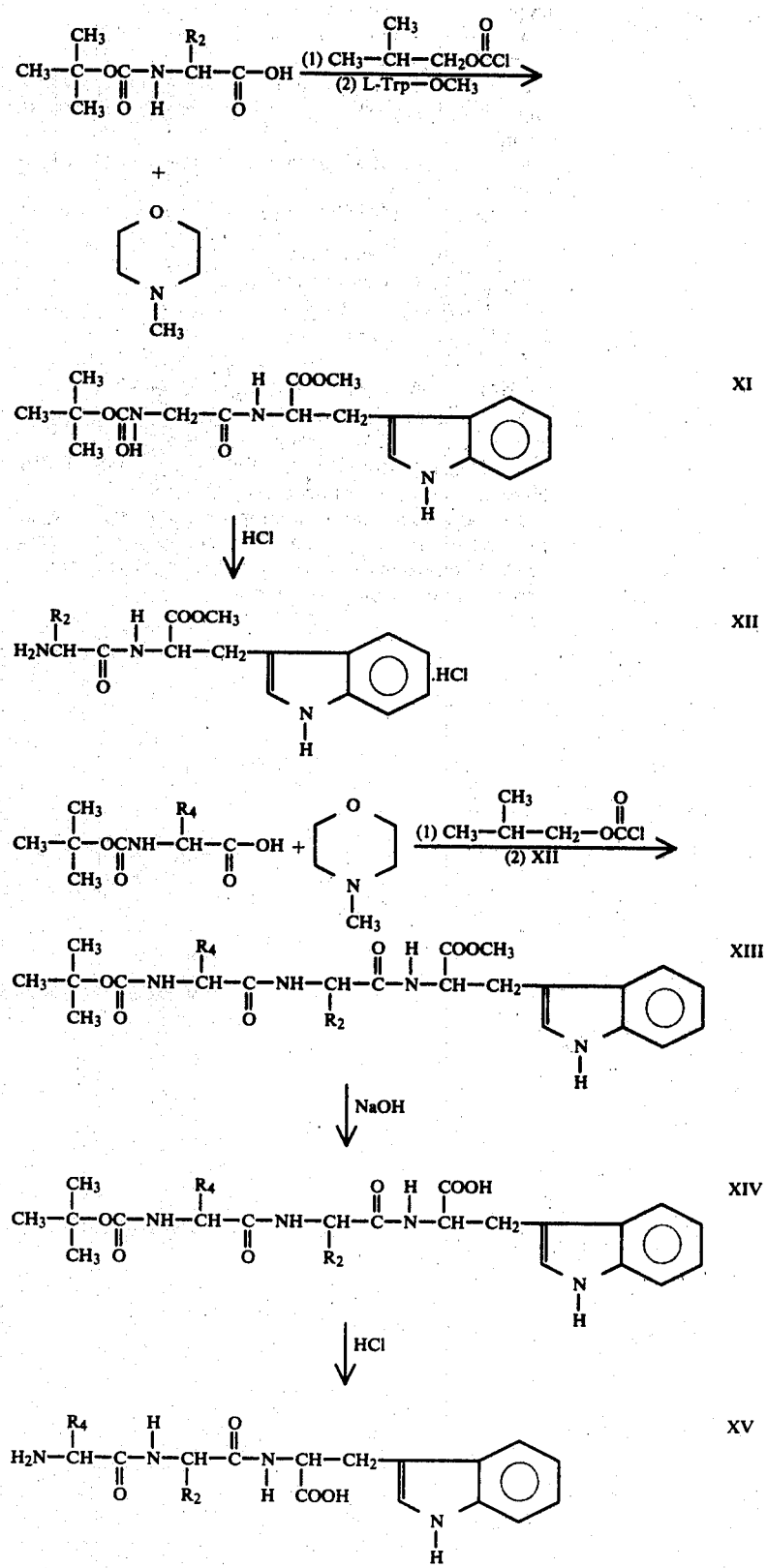
What is claimed is:
1. A compound according to formula I:

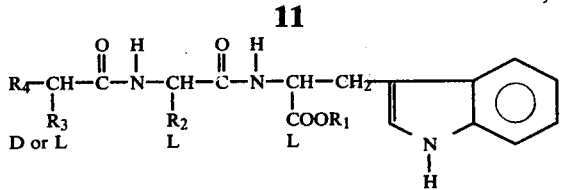

wherein $R_1$ is:
(a) hydrogen;

wherein $R_2$ is:
(a) hydrogen;
(b) iso-propyl; or
(c) tert-butyl;

wherein $R_3$ is:
(a) methyl; or
(b) —$NHR_5$;

whereing $R_5$ is:
(a) hydrogen or
(b) aroyl;

wherein $R_4$ is:
(a) $CH_2SP$;
(b) iso-propyl;
(c) iso-butyl;
(d) imidazolmethyl;
(e) phenylmethyl; or
(f) methylthioethyl;

2. A compound according to claim 1 wherein $R_4$ is —$CH_2SH$.

3. N-[N-(3-mercapto-2-methyl-1-oxopropyl)valyl]-tryptophan, a compound according to claim 2.

4. N-[N-(3-mercapto-2-methyl-1-oxopropyl)glycyl]-tryptophan, a compound according to claim 2.

5. N-[N-(3-mercapto-2-methyl-1-oxopropyl)-3-methylvalyl]tryptophan, a compound according to claim 2.

6. A compound according to claim 1 wherein $k_3$ is —$NH_2$.

7. Leucyl-valyl-tryptophan monohydrochloride, a compound according to claim 6.

8. L-Histidyl-L-valyl-L-tryptophan dihydrochloride, a compound according to claim 6.

9. Valyl-valyl-tryptophan hydrochloride a compound according to claim 6.

10. L-Isoleucyl-L-valyl-L-tryptophan monohydrochloride, a compound according to claim 6.

11. L-Methionyl-L-valyl-L-tryptophan hydrochloride, a compound according to claim 6.

12. L-Leucyl-3-methyl-L-valyl-L-tryptophan hydrochloride, a compound according to claim 6.

13. β-(methylthio-α-aminopropanoyl-valyl)-tryptophan hydrochloride, a compound according to claim 6.

14. Phenylalanyl-valyl-tryptophan hydrochloride, a compound according to claim 6.

* * * * *